(12) United States Patent
Banks

(10) Patent No.: US 8,202,536 B2
(45) Date of Patent: Jun. 19, 2012

(54) METHODOLOGY AND APPARATUS FOR ORAL DUAL DELIVERY OF HOMEOPATHIC PRODUCTS AND NON-HOMEOPATHIC PRODUCTS

(75) Inventor: Brian S. Banks, Dillon, CO (US)

(73) Assignee: Dual Delivery, LCC, Reno, NV (US)

( * ) Notice: Subject to any disclaimer, the term of this patent is extended or adjusted under 35 U.S.C. 154(b) by 78 days.

(21) Appl. No.: 12/777,200

(22) Filed: May 10, 2010

(65) Prior Publication Data

US 2010/0221332 A1    Sep. 2, 2010

Related U.S. Application Data

(62) Division of application No. 12/357,292, filed on Jan. 21, 2009.

(51) Int. Cl.
*A61K 9/20* (2006.01)

(52) U.S. Cl. .......................................... 424/464

(58) Field of Classification Search ................... None
See application file for complete search history.

(56) References Cited

U.S. PATENT DOCUMENTS

2008/0146677 A1* 6/2008 Warnock et al. ............. 514/770
* cited by examiner

*Primary Examiner* — Qiuwen Mi
(74) *Attorney, Agent, or Firm* — John D. Long

(57) ABSTRACT

One possible embodiment of the invention may be an oral dosage apparatus comprising of a sealed, digestible container having an exterior that defines and seals a respective interior; the interior containing one or more non-homeopathic remedies; and the exterior presenting one or more homeopathic products. Another version of the invention may be a method of manufacturing an oral dosage apparatus comprising of the following steps of providing one or more non-homeopathic remedies and one or more non-homeopathic remedies; providing a sealed, digestible container having an exterior that correspondingly defines and seals a respective interior containing one or one or more non-homeopathic remedies; affixing one or more homeopathic remedies to the exterior.

18 Claims, 4 Drawing Sheets

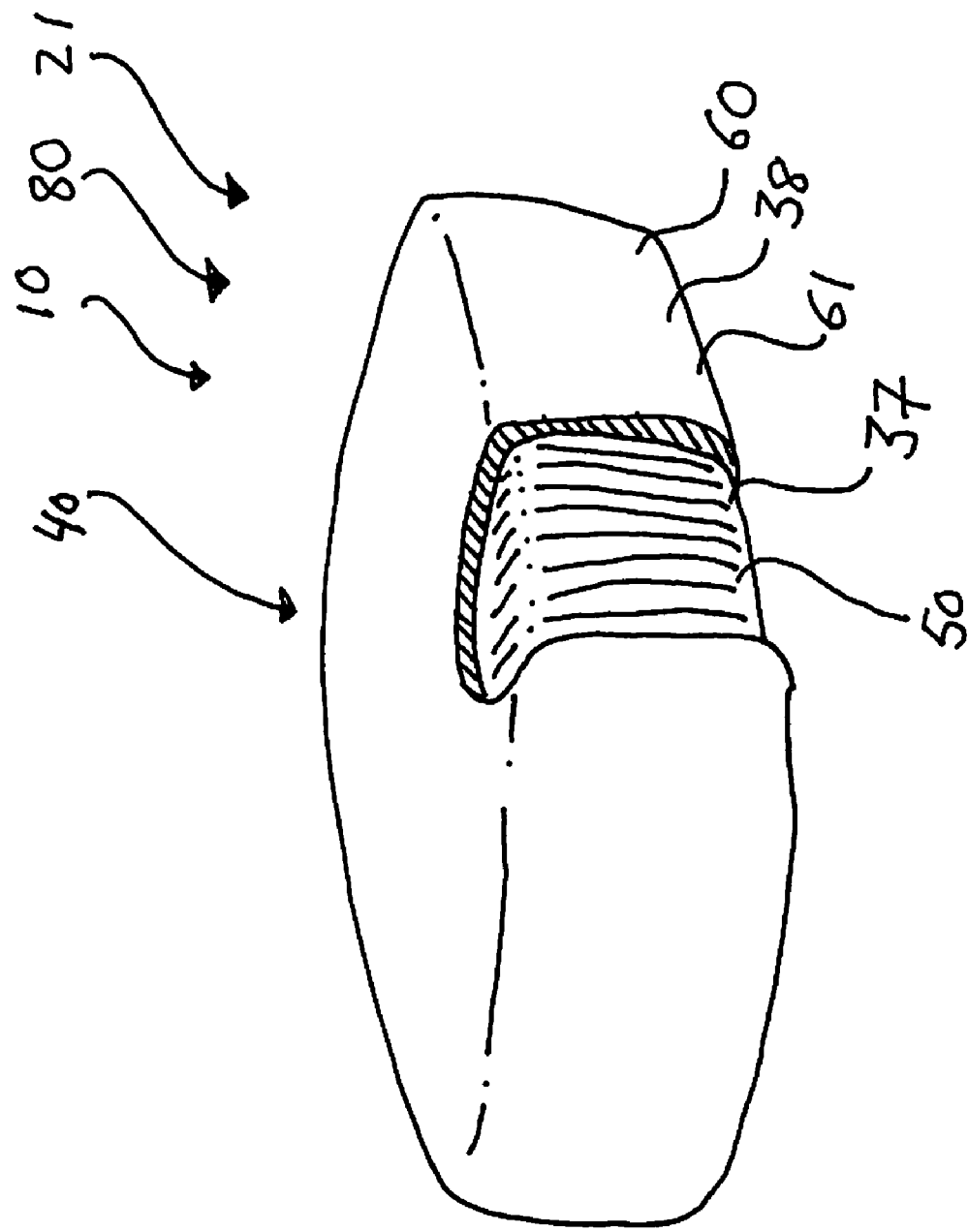

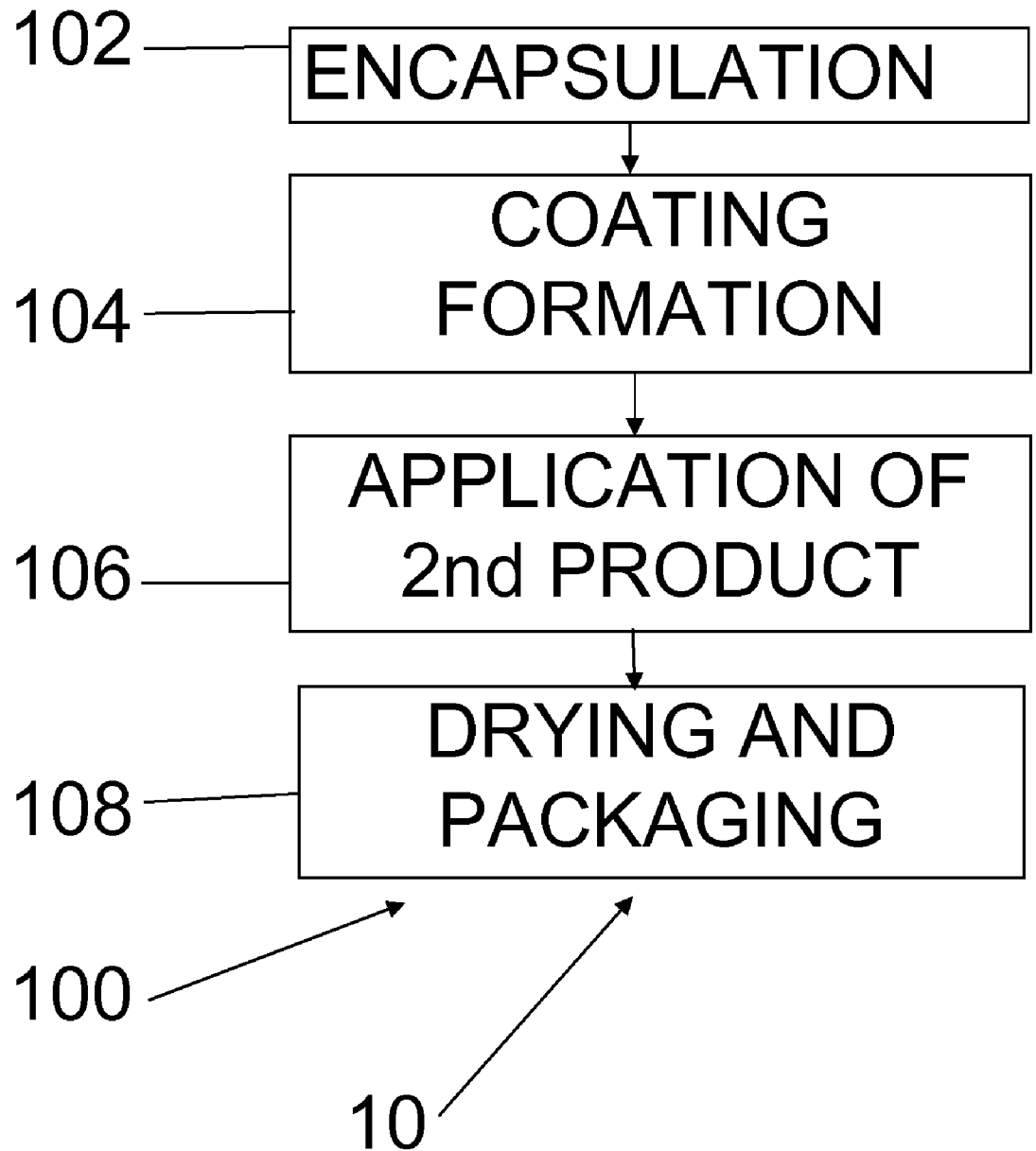

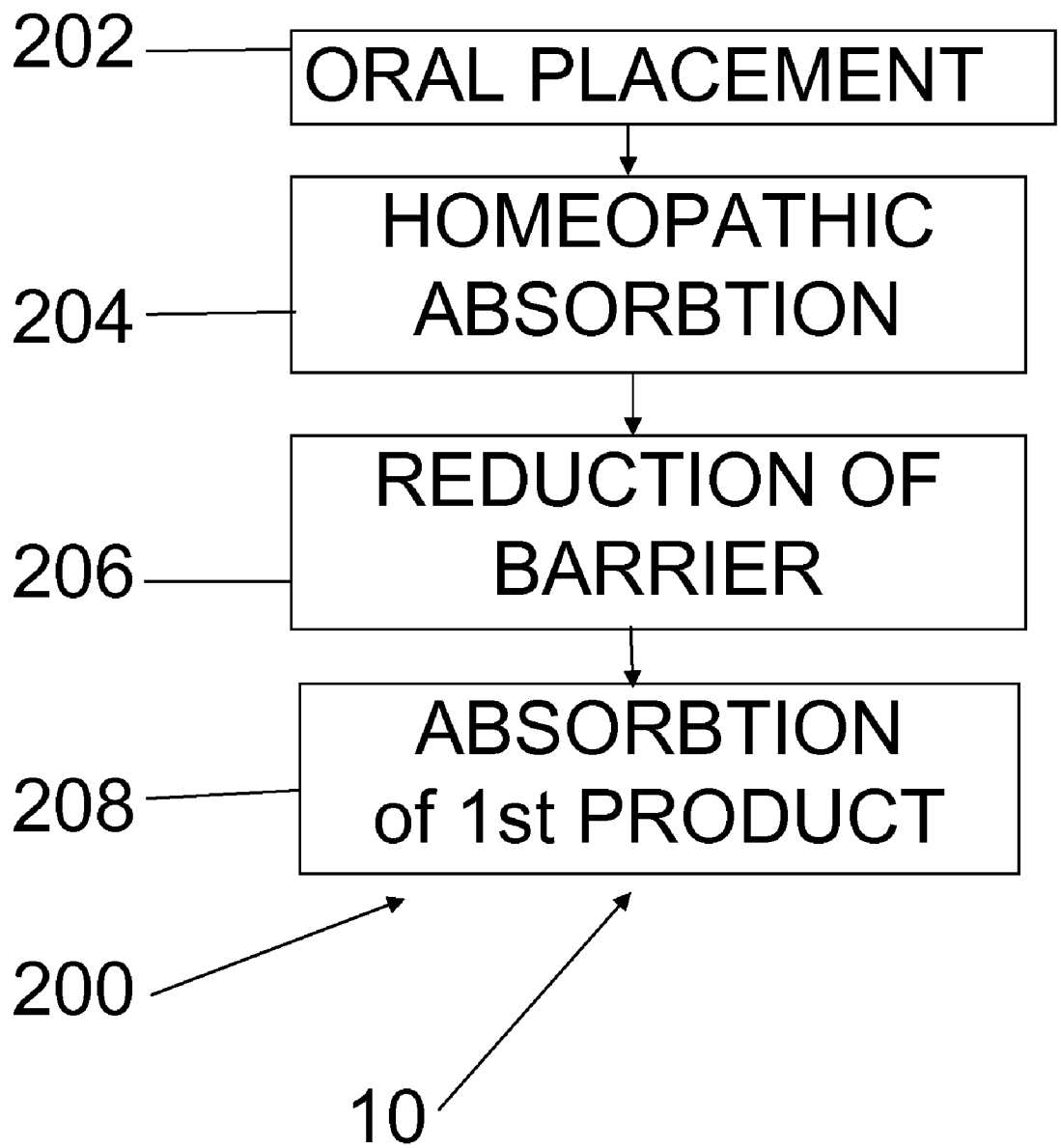

METHODOLOGY AND APPARATUS FOR ORAL DUAL DELIVERY OF HOMEOPATHIC PRODUCTS AND NON-HOMEOPATHIC PRODUCTS

CROSS-REFERENCES TO RELATED APPLICATIONS

The present application claims the benefit under 35 U.S.C. §119(e) of U.S. Provisional Patent Application No. 61/022,402, filed on Jan. 21, 2008 and claims the benefit under 35 U.S.C. §119(e) of said U.S. Provisional Patent Application, the contents of which are relied upon and incorporated by reference. The present application is the divisional application of the U.S. Non-provisional patent application Ser. No. 12/357,292 filed on Jan. 21, 2009 and claims the benefit under 35 U.S.C. §119(e) of said U.S. Non-provisional Patent Application and U.S. Provisional Patent Application, the contents of which are relied upon and incorporated by reference.

STATEMENT REGARDING FEDERALLY SPONSORED RESEARCH OR DEVELOPMENT

Not Applicable

REFERENCE TO A "MICROFICHE APPENDIX"

Not Applicable.

FIELD OF THE INVENTION

The present invention may relate to oral dosage apparatuses, in particular to such apparatuses that provide for simultaneous ingestion but separate absorption of multiple health products.

BACKGROUND

There is a continued consumer interest in the use and development of non-conventional medicines that can be seen as complementary to those remedies prescribed by the practitioners of conventional medicine. One such field of complementary non-conventional medicine may be homeopathy, which may use as remedies, formulations, and compositions whose ingredients or elements are generally not used in conventional medicine. Further, such homeopathic formulations may present their active ingredients in concentrations much lower than the concentrations substantially used in conventional medicine pharmaceuticals.

Such homeopathic products or remedies may be composed by the homeopathic practitioner using one or more material medica, a compilation of homeopathic remedies using homeopathic elements listed in the Homeopathic Pharmacopoeia of the United States ("HPUS"). The HPUS is generally recognized the Food and Drug Administration (hereinafter "FDA") of the United States government as its official homeopathic guideline for the classification and regulation in the manufacture of homeopathic medicines.

As part of its oversight of the homeopathic remedy manufacturing, the FDA mandates that homeopathic products be labeled as being a homeopathic remedy and must have one or more corresponding drug claims (e.g., as indicated as for treating a specific ailment or disease.) The FDA does not mandate that pharmaceutical products, while they may not be labeled homeopathic, must be also be marketed with one or more drug claims.

On the other hand, non-homeopathic, non-pharmaceutical products (e.g., dietary supplements and the like) cannot be labeled as being homeopathic and cannot be otherwise associated with drug claims. The non-homeopathic, non-pharmaceutical products (e.g., dietary supplements) can be associated with a more general structure/function claims (e.g., may help or otherwise facilitate the proper operation of an organ such as the eyes or ears). As such, when non-homeopathic, non-pharmaceutical products are mixed with homeopathic products or elements, even as inactive ingredients, the HPUS holds such a mixture is not a homeopathic remedy. Further, the FDA label advertising and label regulations prohibit the resulting mixture from being labeled as being homeopathic or otherwise be marketed or sold in association with drug claims.

There is a possibility that an oral dosage-based homeopathic remedy may be associated with non-homeopathic elements (e.g., pharmaceutical elements and non-pharmaceutical elements such as dietary supplements) and may still legally claim (e.g., be labeled) to be homeopathic and lay forth medical claims if: 1) the overall remedy product is structured to generally keep the homeopathic remedy physically separated from non-homeopathic element(s); 2) allowing for the separate absorption of homeopathic remedy and non-homeopathic elements at different areas or portions of the alimentary canal (e.g., the digestive tract).

If an oral dosage product, which is capable of separating homeopathic elements from non-homeopathic elements, is swallowed, then the homeopathic element or remedy on the surface of the oral dosage product could first be generally delivered and absorbed in the mouth of the user. The remaining non-homeopathic element or product could then be generally separately delivered and absorbed in other portions of the remainder of the alimentary canal (e.g., stomach, small intestine, large intestine, and the like).

What is needed therefore is an oral dosage apparatus and methodology wherein one or more homeopathic remedies are packed in the same delivery apparatus with one or more non-homeopathic elements, but are kept separate from one another to allow for simultaneous ingestion by the user but further providing generally different absorptions; at generally different times; and at generally different locations in the body of the user.

SUMMARY OF ONE EMBODIMENT OF THE INVENTION

Advantages of One or More Embodiments of the Present Invention

The various embodiments of the present invention may, but do not necessarily, achieve one or more of the following advantages:

the ability to allow for the delivery of different products to different parts of the alimentary canal at different times;

to provide an oral dosage apparatus that will allow for absorption of different products at different parts of the alimentary canal;

to provide an oral dosage apparatus that will allow simultaneous ingestion of both homeopathic products and non-homeopathic products but keeps the two types of products separate from one another for separate digestion at different times at different portions of the alimentary canal of the user;

the ability to keep differently FDA categorized products separate while delivering each to a different part of the alimentary canal; and to provide a means for combining homeopathic products with non-homeopathic remedies that will allow simultaneous ingestion by the user and still allow the combination to be associated with drug claims in accordance with FDA guidelines and regulations.

These and other advantages may be realized by reference to the remaining portions of the specification, claims, and abstract.

Brief Description of One Embodiment of the Present Invention

The invention could be an oral dosage apparatus comprising of a sealed, digestible container, the sealed, digestible container having an exterior that defines and seals a respective interior; the interior further contains one or more non-homeopathic remedies; and the exterior presents one or more homeopathic products.

The invention could be a method of manufacturing an oral dosage apparatus comprising of the following steps, providing one or more homeopathic products; providing a sealed, digestible container, the sealed, digestible container further having an exterior that correspondingly defines and seals a respective interior; providing one or more non-homeopathic remedies, the one or more non-homeopathic remedies located within the interior; and affixing one or more homeopathic remedies to the exterior.

The invention could be a method of using an oral dosage apparatus comprising of the steps of providing one or more non-homeopathic remedies within the interior of sealed, digestible container, the sealed, digestible container having an exterior that generally defines the interior; affixing a homeopathic product to the exterior; placing the sealed, digestible container in the mouth portion of an user's alimentary canal; absorbing an effective amount of the homeopathic product in the mouth portion of the user's alimentary canal; and preventing the absorption of an effective amount of the non-homeopathic remedy in the mouth portion.

The above-description sets forth, rather broadly, a summary of one embodiment of the present invention so that the detailed description that follows may be better understood and contributions of the present invention to the art may be better appreciated. Some of the embodiments of the present invention may not include all of the features or characteristics listed in the above summary. There are, of course, additional features of the invention that will be described below and will form the subject matter of claims. In this respect, before explaining at least one preferred embodiment of the invention in detail, it is to be understood that the invention is not limited in its application to the details of the construction and to the arrangement of the components set forth in the following description or as illustrated in the drawings. The invention is capable of other embodiments and of being practiced and carried out in various ways. Also, it is to be understood that the phraseology and terminology employed herein are for the purpose of description and should not be regarded as limiting.

BRIEF DESCRIPTION OF THE DRAWINGS

FIG. 2 is substantially a cutaway cross-section view of another embodiment of the present invention.

FIG. 3 is substantially a flowchart for one possible process for preparing the invention.

FIG. 4 is substantially a flowchart for one possible process for using the invention.

DESCRIPTION OF CERTAIN EMBODIMENTS OF THE PRESENT INVENTION

Figure 1:
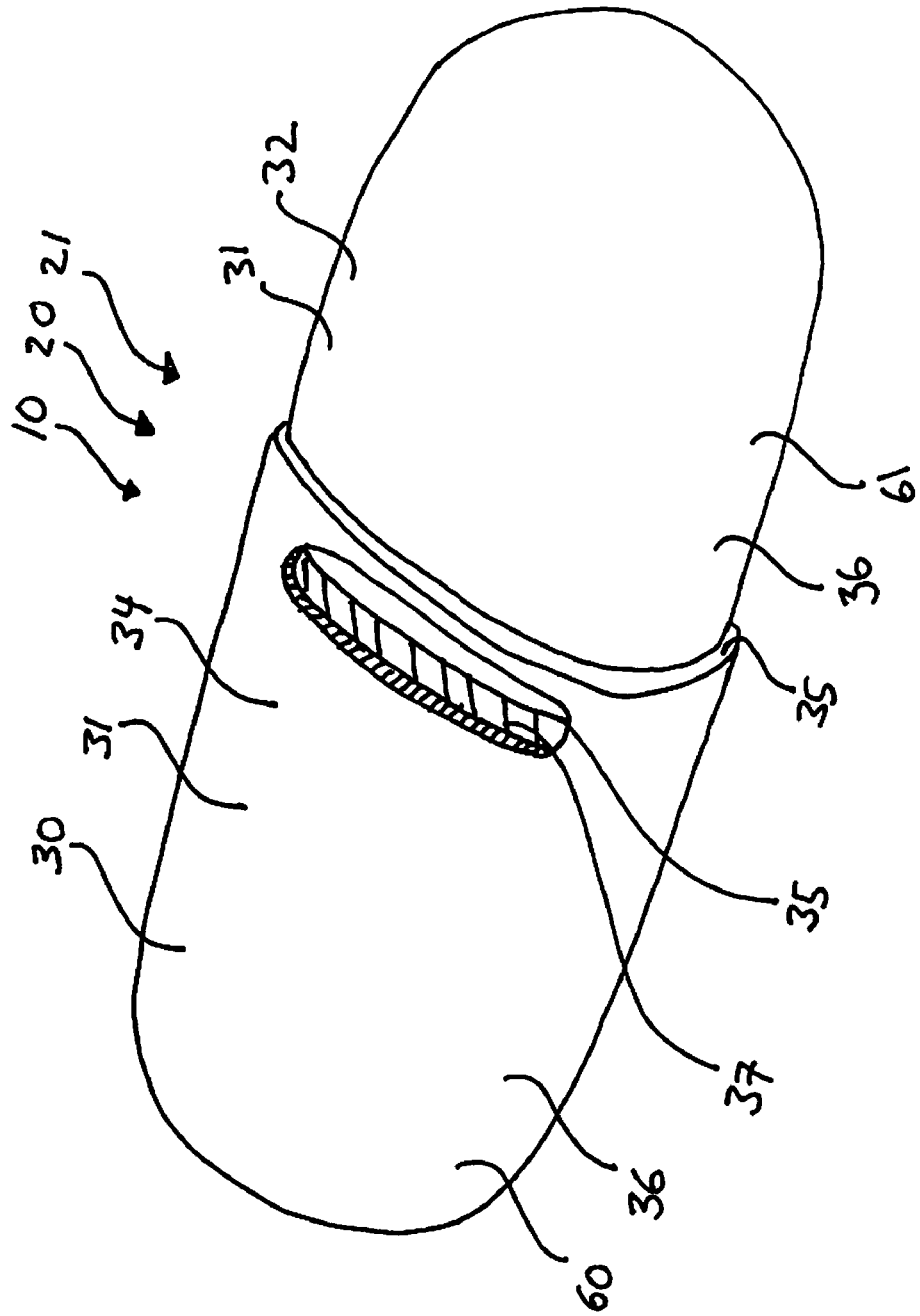
FIG. 1 is substantially a cutaway cross-section view of one embodiment of the present invention.

In the following detailed description of the preferred embodiments, reference is made to the accompanying drawings, which form a part of this application. The drawings show, by way of illustration, specific embodiments in which the invention may be practiced. It is to be understood that other embodiments may be utilized and structural changes may be made without departing from the scope of the present invention.

The invention 10 may comprise an oral dosage apparatus 20; a method of manufacture 100; and a method of use 200 to allow homeopathic products (e.g., HPUS-regulated and FDA-approved homeopathic medicines and remedies) to be combined with non-homeopathic products (such as dietary supplements, pharmaceutical drugs, and the like) and ingested simultaneously but absorbed/digested at different times and at different parts of the alimentary canal of the user.

As generally shown in FIGS. 1 and 2, the oral dosage apparatus 20 could be comprised of sealed digestible container 21 that could present a first product 50 and a second product 60, the structure of the oral dosing apparatus 20 separating the first product 50 from the second product 60. In one embodiment, the sealed, digestible container 21 could generally be gelatin capsule 30 (e.g., gel cap) made of two cup-shaped halves 31 of gelatin or the like. One half (e.g. a first half) 32 could have a lip 35 whose circumference is slightly smaller than the reciprocal lip 35 of its partner half (e.g., second half) 34 that allows the lip 35 of the first half 34 to be generally inserted within that lip 35 of the second half 34. A resulting friction or force fit could then hold the two halves 31 together to generally form a gel capsule 30 having an exterior 36 generally denoting an interior 37 that is otherwise substantially hollow and generally capable of receiving (and subsequently containing) an amount certain of the first product 50, a non-homeopathic product (e.g., dietary supplements, pharmaceutical drugs, and the like.) In the present invention, the dietary supplements could include but not necessarily be limited to a wide variety of herbs, vitamins, herb-vitamin combinations or the like. The actual packaging of the first product 50 into the generally hollow interior 37 of a gel capsule 30 is well within the knowledge of one who has ordinary skills in the art.

As substantially shown, in another embodiment of the invention 10, the first product 50 could be processed into the tablet form with the tablet 40 being further encapsulated by the application of a suitable barrier, coating, seal, or the like 38 to generally denote and otherwise form the exterior 36. In one instance, the barrier coating 38 sealing the tablet 40 could be aqueous methylcellulose. The processing of the first product 50 into a tablet format encapsulated within a barrier coating 38 is well within the knowledge of one having ordinary skill in the art.

Other suitable means for providing the first product placed within other sealed digestible containers 21 could be considered within the purview of the invention 10.

In the various embodiments of the invention 10, the second product 60, a homeopathic product, such as a homeopathic remedy that is normally orally ingested by the patient, could be applied to the exterior 36. The application of the selected second product(s) 60 to the exterior 36 could be accomplished using a traditional carrier agent 61. Such a carrier agent 61 may be an inert ingredient and be selected from a standard, liquidized sugar format, an evaporative alcohol formula or the like.

In one instance, the carrier agent 61 could be impregnated with one or more various second products 60. After the second product 60 is prepared and mixed with the carrier agent 61, a minute amount of this resulting mixture (e.g., the homeopathically impregnated inert material) could be then applied (e.g., sprayed or otherwise coated) upon the exterior 36 of the capsule, tablet, or other chosen sealed, digestible container 21 format.

In another instance, the carrier agent 61 could be first applied to the exterior 36. The second product could then be applied to the previously applied carrier agent 61.

After the carrier agent 61 has set or otherwise evaporated upon the exterior 36 fixing the second product upon the exterior 36, the oral dosage apparatus 20 is generally ready for use.

In utilizing these types of sealed digestible container apparatuses, the invention 10 could generally keep the second product 60 (e.g., homeopathic product) physically separate from the first product 50 (a non-homeopathic product, such as pharmaceutical drugs, dietary supplements, and the like). In this manner, the invention 10, upon ingestion, may first deliver the second product 60 to the mouth and allow it to be absorbed by the body in a traditional oral manner.

The subsequent swallowing or deglutination of the oral dosage apparatus 20 then allows for the first product 50 to be later digested and absorbed in non-mouth portions (s) of the alimentary canal. The invention 10 thus keeps the absorption processes for the two products (i.e., homeopathic and non-homeopathic) separate and independent of the other. The invention 10 can therefor provide for a combination treatment of homeopathic medicine remedy plus non-homeopathic remedy. This may provide a suitable solution for many conditions where there is both a functional disorder amenable both to homeopathic treatment and non-homeopathic treatment.

Additionally, there may be an economic benefit in that the FDA, under its current rules and guidelines, mandates that both homeopathic medicines and pharmaceutical medicines must be marked with drug claims (e.g., that the medicine may help heal specific ailments and diseases). Conversely, the FDA substantially limits dietary supplements (e.g., a wide variety of herbs, vitamins, herb-vitamin combinations or the like) to have weaker structure/function claims (e.g., the item may help a specific part of the body.) By providing an oral dosage delivery system wherein homeopathic remedies are ingested simultaneously with non-homeopathic, non-pharmaceutical remedies but otherwise are generally kept physically separate from one another (and allowing for substantially separate digestion); the resulting product could possibly avail itself of being legally marketed with drug claims.

Methodology of Manufacture

As generally shown in FIG. 3, the process 100 of manufacturing the invention 10 could start with step 102, encapsulation. Here, the first product of the invention (e.g., generally a non-homeopathic remedy such as dietary or nutritional supplement [such as vitamins, herbs, minerals, and the like]; a pharmaceutical remedy; and the like) are selected. In at least one instance, the first product(s) may be tabulated (e.g., placed into a tablet format); encapsulated within a traditional capsule; or otherwise presented into any suitable pill form. If the tablet format is utilized, the tablet(s) could be further coated with an aqueous solution of methylcellulose or other suitable material to provide a coating barrier about the pill to later provide a degree of separation between the first product and the later exteriorly applied second product (e.g., homeopathic medicine.)

Alternatively, the encapsulated first product utilizes the shell of the gelatin capsule to maintain the separation of the first product from the second product. The shell of the gelatin capsule and the seal of the tablet being generally sufficient to prevent an effective amount of the non-homeopathic remedy from being absorbed in the mouth portion of the alimentary canal of the user when coming into contact with said portion. Upon the substantial completion of step one, the process 100 may proceed onto step 104, coating formation.

At step 104, coating formation, a FDA-approved carrying agent for the second product or homeopathic medicine is selected. Such a carrying agent could be a sugar (such as sucrose, lactose, fructose, or the like) or sugar alcohol (e.g., xylitol or the like) that has been converted to a liquid form.

One or more selected homeopathic remedies or medicines (second product) may then be selected (and combined) into a single formula. That formula may then be potentized according to homeopathic principles in liquid format or later converted to a liquid format. The resulting liquid solution could have an aqueous base comprising an 87% ratio of alcohol/water or other suitable ratio as may be needed to flow the second product through the application equipment and to facilitate the drying of its carrier agent upon the surface of the pill. At the close of step two, the process 100 could proceed to step 106, application of the second product.

In step 106, application of the second product, in at least one embodiment, the prepared carrying agent and the homeopathic product (e.g., homeopathic formula, medicine, remedy or the like) may be mixed together. The resulting liquid solution is then applied (e.g., sprayed, painted, or otherwise coated) upon the exterior of the capsule or the pre-coated tablet. In another embodiment, the approved carrying agent is prepared without the homeopathic second product. The carrying agent, sans the homeopathic second product, could be applied to the exterior of the pill. The carrying agent-coated pill could then be impregnated with the homeopathic second product. After generally completing step three, the process 100 could proceed to step 108, drying and packaging.

At step 108, drying and packaging, the invention could have the carrying agent dried according to drying methods known to those with ordinary skill in the art, and then have the invention packaged for subsequent sale using known methods for packaging such items. The packaging of the invention could bear indicia setting forth drug claims for the invention.

Methodology of Use

One possible embodiment of the invention could be a process 200 for using the apparatus starting with step 202: oral placement. In this step, the user could place the apparatus in the user's mouth and move the apparatus around the mouth with the tongue. Upon substantial completion of this step, the process 200 could generally proceed to step 204, homeopathic absorption.

In step 204, homeopathic absorption, the user could permit contact of the apparatus with saliva and mucosal membrane of the user's mouth. This action along with swishing of the invention in the user's mouth could allow at least an effective amount of the homeopathic second product to be transferred from the apparatus and be absorbed in the mouth of the user. The user, after "swishing" the apparatus in the mouth, could commence the act of deglutination or swallowing, thus introducing the remaining apparatus to the esophagus and other non-mouth portions of the alimentary canal, namely the stomach. Upon substantial completion of step 204, the process 200 could proceed to step 206, reduction of the barrier.

In step 206, reduction of the barrier, which may have initially commenced with contact of the pill with the saliva in the mouth, could undergo true and generally complete dissolution and removal of the gelatin capsule or the barrier (e.g., the coating or seal) of the tablet substantially take place in the stomach in the presence of the gastric juices and with the normal churning motion of the stomach. Once the substantial removal of the gelatin capsule or barrier coating surrounding the first product is generally completed, the first product (e.g., the non-homeopathic remedy) can be exposed to the non-mouth portion of the alimentary canal. Upon completion of step three, the process can proceed to step 208, absorption of the first product.

At step 208, absorption of the first product, the exposed first product could make contact with the remaining portion of the alimentary canal such as the stomach lining, the mucosa of the intestine, and the like. Depending on the nature of the first product, the exposed first product can generally be absorbed by the mucosa of other non-mouth parts of the alimentary canal (e.g., stomach, intestine and the like.)

Conclusion

The invention could allow homeopathic medicines and remedies and non-homeopathic products to be simultaneously present but separated in a dual stage oral dosing apparatus allowing for simultaneous ingestion but separate absorption of the different types of products in different parts of the alimentary canal at different times. The two types of products could complementarily treat the same health issues or address different health issues.

The structure of the invention, in keeping the two types of remedies separate, could possibly provide an economic benefit to have the oral dosing apparatus providing a combination of both homeopathic and non-homeopathic, non-pharmaceutical products be marketed with medical claims that normally are not otherwise allowed by under FDA guidelines and regulations.

Although the description above contains many specifications, these should not be construed as limiting the scope of the invention but merely as providing illustrations of some of the presently preferred embodiments of this invention. Thus, the scope of the invention should be determined by their legal equivalents rather than just by the examples given.

The invention claimed is:

1. A method of using an oral dosage apparatus comprising of the steps, but not necessarily in the order shown:
   (A) providing one or more non-homeopathic remedies contained within an interior of a sealed digestible container, the sealed digestible container having an exterior that generally defines and seals the interior;
   (B) providing at least one homeopathic product that is affixed to the exterior of the sealed digestible container in a manner that keeps the at least one homeopathic product separate and apart from the one or more non-homeopathic remedies contained within the interior of the sealed digestible container to form an oral dosage apparatus;
   (C) placing the oral dosage apparatus in a mouth portion of an user's alimentary canal;
   (D) absorbing an effective amount of at least one homeopathic product in the mouth portion of the user's alimentary canal;
   (E) preventing absorption of an effective amount of one or more the non-homeopathic remedies in the mouth portion of the user's alimentary canal; and
   (F) selling the oral dosage apparatus as a homeopathic product containing one or more non-homeopathic remedies and further associating the oral dosage apparatus with one or more drug claims.

2. The method of claim 1 further comprising of a step of swallowing the sealed digestible container to deliver it to a non-mouth portion of the alimentary canal.

3. The method of claim 2 further comprising of a step of preventing absorption of an effective amount of at least one homeopathic product in the non-mouth portion of the user's alimentary canal.

4. The method of claim 2 further comprising of a step of absorbing an effective amount of a non-homeopathic remedy in a non-mouth portion of the alimentary canal while preventing absorption of an effective amount of at least one homeopathic product in the non-mouth portion of the user's alimentary canal.

5. The method of claim 4 wherein the step of absorbing an effective amount of the non-homeopathic remedy of the non-mouth portion of the alimentary canal is done at a different time than the absorbing an effective amount of at least one homeopathic product in the mouth portion of the user's alimentary canal.

6. The method of claim 3 wherein the step of preventing of the absorption of an effective amount of the at least one homeopathic product in the non-mouth portion of the user's alimentary canal is done at a different time than the preventing the absorption of an effective amount of the non-homeopathic remedy of the mouth portion.

7. The method of claim 1 wherein the at least one homeopathic product is affixed by the step of forming a mixture of one or more homeopathic remedies and a carrier agent and then applying the resulting mixture to the exterior.

8. The method of claim 1 wherein the at least one homeopathic product is affixed by a step of applying the carrier agent to the exterior and then of the step of applying the one or more homeopathic remedies to the carrier agent-covered exterior.

9. The method of manufacturing of claim 1 further comprising of a step of providing a sealed digestible container by applying methylcellulose to a tablet containing non-homeopathic remedies.

10. A method of using an oral dosage apparatus comprising of the steps, but not necessarily in the order shown:
    (A) providing oral dosage apparatus comprising of a sealed digestible container, the sealed digestible container having an exterior that generally defines the interior containing one or more non-homeopathic remedies and at least one homeopathic product applied to the exterior of the sealed digestible container;
    (B) placing the oral dosage apparatus in a mouth portion of an user's alimentary canal;
    (C) absorbing an effective amount of at least one homeopathic product in the mouth portion of the user's alimentary canal; and
    (D) preventing absorption of an effective amount of one or more the non-homeopathic remedies in the mouth portion of the user's alimentary canal; and
    (E) selling the oral dosage apparatus as a homeopathic remedy with one or more drug claims.

11. The method of claim 10 further comprising of a step of delivering the sealed digestible container to a non-mouth portion of the alimentary canal.

12. The method of claim 10 further comprising of the step of the absorbing an effective amount of a non-homeopathic remedy in the non-mouth portion of the alimentary canal.

13. The method of claim 10 further comprising of the step of preventing an absorption of an effective amount of one or more the homeopathic products in the non-mouth portion of the user's alimentary canal.

14. The method of claim 10 wherein the absorbing an effective amount of the homeopathic product in the mouth portion of the user's alimentary canal is done at a different time than the absorbing an effective amount of the non-homeopathic remedy of the non-mouth portion.

15. The method of claim 12 wherein affixing at least one homeopathic product further comprises of the step of forming a mixture of one or more homeopathic remedies and a carrier agent and then applying the resulting mixture to the exterior.

16. A method of using an oral dosage apparatus comprising of the following steps, but not necessarily in the order shown:
    (A) providing a sealed, digestible container, the sealed, digestible container further having an exterior that correspondingly defines and seals a respective interior;
    (B) providing one or more non-homeopathic remedies, the one or more non-homeopathic remedies located within the interior;
    (C) providing one or more homeopathic remedies that are affixed to the exterior to form an oral dosage apparatus; and
    (D) selling the oral dosage apparatus as a homeopathic product with one or more drug claims.

17. The method of claim 16 further comprising of a step of ingesting the oral dosage device to absorb an effective amount of one or more the non-homeopathic remedies in the non-mouth portion of the user's alimentary canal while simultaneously preventing absorption of an effective amount of at least one homeopathic product in the non-mouth portion of the user's alimentary canal.

18. The method of claim 17 wherein the preventing of absorption of the effective amount of one or more the non-homeopathic remedies in the mouth portion of the user's alimentary canal occurs at a different time than the step of preventing the absorption of the effective amount of at least one homeopathic remedies in the non-mouth portion of the user's alimentary canal.

* * * * *